US012576019B2

(12) United States Patent
Wei et al.

(10) Patent No.: US 12,576,019 B2
(45) Date of Patent: Mar. 17, 2026

(54) PERSONAL CLEANSING COMPOSITION WITH AN ORGANIC ACID HAVING A pKa GREATER THAN 2.7

(71) Applicant: The Procter & Gamble Company, Cincinnati, OH (US)

(72) Inventors: Karl Shiqing Wei, Mason, OH (US); Lesheng Zhang, Beijing (CN); Xiaojian Wu, Beijing (CN); Hechuan Yu, Beijing (CN); Jessa Leigh Meyers, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 556 days.

(21) Appl. No.: 17/975,668

(22) Filed: Oct. 28, 2022

(65) Prior Publication Data

US 2023/0135226 A1     May 4, 2023

(30) Foreign Application Priority Data

Oct. 29, 2021   (WO) ................ PCT/CN2021/127315
Oct. 29, 2021   (WO) ................ PCT/CN2021/127318

(51) Int. Cl.

| | |
|---|---|
| *A61K 8/00* | (2006.01) |
| *A61K 8/36* | (2006.01) |
| *A61K 8/44* | (2006.01) |
| *A61K 8/46* | (2006.01) |
| *A61Q 19/10* | (2006.01) |

(52) U.S. Cl.
CPC ................ *A61K 8/463* (2013.01); *A61K 8/36* (2013.01); *A61K 8/44* (2013.01); *A61Q 19/10* (2013.01); *A61K 2800/5424* (2013.01); *A61K 2800/74* (2013.01)

(58) Field of Classification Search
None
See application file for complete search history.

(56) References Cited

U.S. PATENT DOCUMENTS

| | | | |
|---|---|---|---|
| 10,357,442 B2 | 7/2019 | Schelges et al. | |
| 10,441,522 B2 | 10/2019 | Schelges et al. | |
| 11,160,741 B2 | 11/2021 | Guskey et al. | |
| 11,191,705 B2 | 12/2021 | Wang et al. | |
| 2013/0172415 A1 | 7/2013 | Vermeulen et al. | |
| 2021/0302408 A1 | 9/2021 | Wei et al. | |

FOREIGN PATENT DOCUMENTS

| | | |
|---|---|---|
| CN | 103349622 A | 10/2013 |
| CN | 104921989 A | 9/2015 |
| CN | 107468563 A | 12/2017 |
| CN | 110025519 A | 7/2019 |
| CN | 110327282 A | 10/2019 |
| CN | 112206176 A | 1/2021 |
| EP | 2090291 A1 | 8/2009 |
| EP | 3329904 A1 | 6/2018 |
| JP | 2014114291 A * | 6/2014 |
| WO | 2004000016 A2 | 12/2003 |
| WO | 2005105070 A2 | 11/2005 |
| WO | 2009100999 A1 | 8/2009 |
| WO | 2010069500 A1 | 6/2010 |
| WO | 2015058942 A1 | 4/2015 |
| WO | 2017055789 A2 | 4/2017 |
| WO | 2020055562 A1 | 3/2020 |
| WO | 2020144125 A1 | 7/2020 |

OTHER PUBLICATIONS

Anonymous, "Pure Freesia Amino Acid Antibacterial Bath Essence", Database GNPD [Online] Mintel, Aug. 20, 2020, 3 pages.
PCT Search Report and Written Opinion for PCT/CN2021/127315 dated May 3, 2022, 11 pages.
Lambers H et al., "Natural skin surface Ph is on average below 5, which is beneficial for its resident flora", International Journal of Cosmetic Science, vol. 28, No. 5, Sep. 19, 2006, pp. 359-370.

* cited by examiner

*Primary Examiner* — Necholus Ogden, Jr.
(74) *Attorney, Agent, or Firm* — Alexandra S. Anoff; Matthew J. Spegele

(57) ABSTRACT

A personal cleansing composition includes from about 1% to about 15% of an anionic surfactant by weight of the composition, wherein the anionic surfactant comprises sodium laureth(n) sulfate (SLEnS), wherein n is the average moles of ethoxylation, wherein n equals to 1, 2 or 3; from about 0.01% to about 1% of an organic acid having a pKa greater than about 2.7, or a cosmetically acceptable salt thereof, or a mixture thereof, by weight of the composition; and wherein the pH of the personal cleansing composition is from about 5.0 to about 6.5.

10 Claims, No Drawings

PERSONAL CLEANSING COMPOSITION WITH AN ORGANIC ACID HAVING A pKa GREATER THAN 2.7

FIELD OF THE INVENTION

The present application generally relates to personal cleansing compositions, their non-therapeutic methods for improving or maintaining the natural defensive ability of human skin against bacteria, in particular *Staphylococcus aureus*, and their uses. The personal cleansing compositions have desirable properties for helping skin maintain or improve its natural barrier against bacteria, especially *Staphylococcus aureus*, and retaining moisture due to the use of an organic acid having a pKa greater than about 2.7 at a certain pH from about 3.0 to about 6.5.

BACKGROUND OF THE INVENTION

Personal cleansing compositions have been traditionally marketed in a variety of forms such as bar soaps, creams, lotions, and gels. Typically, these products need to satisfy a number of criteria to be acceptable to consumers. These criteria include cleansing effectiveness, skin feel, mildness to skin, hair, and ocular mucosae, and lather volume. Ideal personal cleansers should gently cleanse the skin or hair, cause little or no irritation, and should not leave the skin or hair overly dry after frequent use.

Skin provides the first line of defense against bacteria. Healthy skin contains natural moisturizing factors (NMF). In addition to helping skin retain moisture, NMF can also act as a buffer that can help skin retain its acid mantle. The acid mantle is a very fine, slightly acidic film on the skin that acts as a barrier to bacteria. Cleansing products but also other insults to skin barrier such as aging, UV radiation can alter the skin barrier and the content of NMF. When NMF is lost, the acid mantle is disrupted and the skin barrier is weakened, which can lead to dry cracked skin and can compromise skin's ability to protect against bacteria.

Therefore, there is a need for a personal cleansing product that effectively maintain or improve skin's acid mantle and its ability to defend against bacteria. There is also a need for a non-therapeutic method for helping human skin maintain its natural defensive ability against bacteria and that effectively maintain skin's acid mantle.

SUMMARY OF THE INVENTION

A personal cleansing composition is provided and comprises:
  (a) from about 1% to about 15% of an anionic surfactant by weight of the composition, wherein the anionic surfactant comprises sodium laureth(n) sulfate SLEnS, wherein n is the average moles of ethoxylation, wherein n equals to 1, 2 or 3, preferably sodium laureth(n) sulfate SLEnS, wherein n is the average moles of ethoxylation, wherein n equals to 1;
  (b) from about 0.01% to about 1% of an organic acid having a pKa greater than about 2.7, preferably a pKa from about 2.75 to about 5, more preferably a pKa from about 3 to about 4.5, or a cosmetically acceptable salt thereof, or a mixture thereof, by weight of the composition; and
  wherein the pH of the personal cleansing composition is from about 5.0 to about 6.5.
The personal cleansing composition as set out hereinbefore is used for maintaining or improving the natural defensive ability of human skin against bacteria, preferably for maintaining or improving the natural defensive ability of human skin against *Staphylococcus aureus*.

The personal cleansing composition as set out hereinbefore is used for promoting the skin natural defense efficacy.

The personal cleansing composition as set out hereinbefore is used for maintaining or restoring the natural skin pH.

The personal cleansing composition as set out hereinbefore is used for balancing skin pH and retaining skin moisture.

A method for maintaining or improving the natural defensive ability of human skin against bacteria, preferably against *Staphylococcus aureus*, comprising the step of applying onto the human skin the personal cleansing composition as set out hereinbefore, following by rinsing off the composition.

A method for promoting the skin natural defense efficacy comprising the step of applying onto the human skin the personal cleansing composition as set out hereinbefore, following by rinsing off the composition.

A method for maintaining or restoring the natural skin pH comprising the step of applying onto the human skin the personal cleansing composition as set out hereinbefore, following by rinsing off the composition.

A non-therapeutic method for helping human skin maintain, or enhance, its natural defensive ability against bacteria, especially *Staphylococcus aureus* is provided and comprises the step of applying onto the human skin a personal cleansing composition following by rinsing off the composition;
  wherein the personal cleansing composition comprises:
    (a) from about 1% to about 20% of an anionic surfactant by weight of the composition, wherein the anionic surfactant comprises an anionic amino acid surfactant and/or sodium laureth(n) sulfate SLEnS, wherein n is the average moles of ethoxylation, wherein n equals to 1, 2 or 3;
    (b) from about 0.01% to about 1% of an organic acid having a pKa greater than about 2.7, preferably a pKa from about 2.75 to about 5, more preferably a pKa from about 3 to about 4.5, or a cosmetically acceptable salt thereof, or a mixture thereof, by weight of the composition; and
  wherein the pH of the personal cleansing composition is from about 3.0 to about 6.5.
The personal cleansing composition as set out hereinbefore is used for helping skin maintain, or enhance, its natural barrier against bacteria, especially *Staphylococcus aureus*.

DETAILED DESCRIPTION OF THE INVENTION

Definitions of Terms

In this document, including in all embodiments of all aspects of the present invention, the following definitions apply unless specifically stated otherwise.

All percentages are by weight (w/w) of the composition, unless otherwise specified. "% wt." means percentage by weight. References to 'parts' e.g. a mixture of 1 part X and 3 parts Y, is a ratio by weight. All ratios or percentages are weight ratios or weight percentages unless specifically stated otherwise.

An "active composition" is the composition absent water, and an "active ingredient" is the ingredient absent its water.

"QS" or "QSP" means sufficient quantity for 100% or for 100 g. +/− indicates the standard deviation. All ranges are inclusive and combinable. The number of significant digits conveys neither a limitation on the indicated amounts nor on the accuracy of the measurements. All numerical amounts are understood to be modified by the word "about".

All measurements are understood to be made at 25° C. and at ambient conditions, where "ambient conditions" means at 1 atmosphere (atm) of pressure and at 65% relative humidity, unless otherwise stated. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International.

Herein "min" means "minute" or "minutes". Herein "mol" means mole. Herein "g" following a number means "gram" or "grams". "Ex." means "example". All amounts as they pertain to listed ingredients are based on the active level and do not include carriers or by-products that may be included in commercially available materials.

Herein, "comprising" means that other steps and other ingredients can be in addition. "Comprising" encompasses the terms "consisting of" and "consisting essentially of". The compositions, methods, uses, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated.

As used herein, the articles including "a" and "an" when used in a claim, are understood to mean "one or more" of what is claimed or described.

The terms "include," "includes," and "including," as used herein are meant to be non-limiting.

Where amount ranges are given, these are to be understood as being the total amount of said ingredient in the composition, or where more than one species fall within the scope of the ingredient definition, the total amount of all ingredients fitting that definition, in the composition.

For example, if the composition comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the composition.

The term "free of" as used herein means that the composition comprises 0% of an ingredient by weight of the composition, thus no detectable amount of the stated ingredient.

The term "substantially free of" as used herein means less than about 1%, less than about 0.8%, less than about 0.5%, less than about 0.3%, or less than an immaterial amount of by weight of the composition.

Herein "Comp. Ex." or "C. Ex." means comparative example; and "Ex." means example.

The term "molecular weight" or "M·Wt." as used herein refers to the weight average molecular weight unless otherwise stated. The weight average molecular weight can be measured by gel permeation chromatography ("GPC").

The term "personal cleansing composition" as used herein refers to compositions intended for topical application to the skin for cleansing.

The term "mixtures" as used herein is meant to include a simple combination of materials and any compounds that may result from their combination.

The term "room temperature" refers to a temperature of 25° C.

The term "rinse-off" as used herein means the intended product usage includes application to skin followed by rinsing and/or wiping the product from the skin within a few seconds to minutes of the application step. The product is generally applied and rinsed in the same usage event, for example, a shower or washing one's hands.

The term "derivative" as used herein refers to structures which are not shown but which one skilled in the art would understand are variations of the basic compound.

The methods as disclosed herein are cosmetic methods or non-therapeutic methods.

The objects of the present invention are to provide personal cleansing products, methods and uses of the products, the structures and the respective compositions as described in the Summary or as described hereinbelow for fulfilling the technical effects or goals as set out herein. These objects and other advantages as may be apparent to those skilled in the art can be achieved through the present invention, which is described in the above Summary of the Invention and Detailed Description of the invention and which is defined in the claims which follow.

Method

A non-therapeutic method for helping human skin maintain, or enhance, its natural barrier against bacteria is provided and comprises the step of applying onto the human skin a personal cleansing composition as set out hereinafter, following by rinsing off the composition.

Benefits

Human skin is the body's largest organ and is part of the body's natural defense to microbial attack. The natural skin defense is made up of a multitude of components. For example, the skin's natural defense includes the skin's ability to be a physical barrier, the pH of the skin, the skin microbiome, lipids on the skin, chemical components of the skin, etc.

Human skin's ability to provide a natural defense against microbial attack can be impacted by things with which it comes into contact during the day, like skin products. Bacteria does not only stay on the skin surface, but also go deep into skin. It compromises skin barrier, causing skin sensitivity and irritation.

It was found that a personal cleansing composition that can contain an anionic surfactant wherein the anionic surfactant comprises an anionic amino acid surfactant and/or sodium laureth(n) sulfate (SLEnS), wherein n is the average moles of ethoxylation, wherein n equals to 1, 2 or 3 and an organic acid having a pKa greater than about 2.7 can effectively help balance skin pH to maintain or enhance skin's acid mantle and its ability to defend against bacteria.

It was found that certain organic acid having a specific pKa can contribute to human skin's protective layer to maintain, or enhance, the skin's acid mantle and maintain its ability to defend against bacteria.

It is believed that an organic acid having a specific pKa greater than about 2.7, alternatively a pKa from about 2.75 to about 5, alternatively a pKa from about 3 to about 4.5, as set out hereinafter can penetrate at least three layers into the skin, which can provide a deep layer of protection to users for at least about 12 hours, alternatively for at least about 6 hours, alternatively for at least about 4 hours.

Testing of the skin's natural defense can be performed according to the Method for Measuring Residual Antimicrobial Efficacy of a Product, described herein. *Staphylococcus aureus* is a logarithmic scale, measured in colony-forming unit (CFU). DT is a logarithmic scale, which corresponds to level of bacteria.

The personal cleansing composition has a pH from about 3.0 to about 6.5, alternatively from about 4.0 to about 5.8, alternatively from about 4.5 to about 5.7, alternatively from about 4.7 to about 5.7, alternatively from about 5.0 to about 6.5, alternatively from about 5.2 to about 6.0, alternatively from about 5.3 to about 5.8, alternatively from about 5.4 to about 5.8, alternatively from about 5.5 to about 5.7. pH is measured according to the Product pH Measurement Test Method, described hereafter.

The personal cleansing composition may have a viscosity from about 2.75 Pa·s (about 2750 cps) to about 15 Pa·s (about 15,000 cps), alternatively from about 3 Pa·s (about 3000 cps) to about 13 Pa·s (about 13,000 cps), alternatively from about 4 Pa·s (about 4000 cps) to about 11 Pa·s (about 11,000 cps), alternatively from about 5 Pa·s (about 5000 cps) to about 10 Pa·s (about 10,000 cps), and alternatively from about 6 Pa·s (about 6000 cps) to about 10 Pa·s (about 9000 cps), according to the Cone/Plate Viscosity Measurement, described herein.

Anionic Surfactant

The personal cleansing composition includes an anionic surfactant. Anionic surfactants can provide a cleaning benefit, lather properties, and rheology properties to the compositions.

The personal cleansing composition comprises from about 1% to about 20%, alternatively from about 1% to about 15%, alternatively from about 3% to about 13%, alternatively about from 5% to about 13%, alternatively from about 8% to about 12%, alternatively from about 9% to about 11%, or alternatively from about 9% to about 10%, by weight of the composition, of an anionic surfactant.

The anionic surfactant comprises an anionic amino acid surfactant. The anionic amino acid surfactant may be selected from the group consisting of a taurate surfactant, a glutamate surfactant, an alaninate surfactant, a sarcosinate surfactant, an aspartate surfactant, a glycinate surfactant, and mixtures thereof. Alternatively, the anionic amino acid surfactant may be selected from the group consisting of an alaninate surfactant, a sarcosinate surfactant, and mixtures thereof.

The taurate surfactant may be selected from the group consisting of potassium cocoyl taurate, potassium methyl cocoyl taurate, sodium caproyl methyl taurate, sodium cocoyl taurate, sodium lauroyl taurate, sodium methyl cocoyl taurate, sodium methyl lauroyl taurate, sodium methyl myristoyl taurate, sodium methyl oleoyl taurate, sodium methyl palmitoyl taurate, sodium methyl stearoyl taurate, and mixtures thereof.

In some examples, the taurate surfactant may be selected from the group consisting of potassium cocoyl taurate, potassium methyl cocoyl taurate, sodium caproyl methyl taurate, sodium cocoyl tau rate, sodium lauroyl taurate, sodium methyl cocoyl taurate, sodium methyl lauroyl taurate, and mixtures thereof. In other examples, the taurate surfactant may be selected from the group consisting of potassium cocoyl taurate, potassium methyl cocoyl taurate, sodium cocoyl taurate, sodium lauroyl taurate, sodium methyl cocoyl taurate, sodium methyl lauroyl taurate, and mixtures thereof.

The glutamate surfactant may be selected from the group consisting of sodium cocoyl glutamate, disodium cocoyl glutamate, ammonium cocoyl glutamate, diammonium cocoyl glutamate, sodium lauroyl glutamate, disodium lauroyl glutamate, sodium cocoyl hydrolyzed wheat protein glutamate, potassium cocoyl glutamate, potassium lauroyl glutamate, potassium cocoyl hydrolyzed wheat protein glutamate, sodium capryloyl glutamate, disodium capryloyl glutamate, potassium capryloyl glutamate, dipotassium capryloyl glutamate, sodium undecylenoyl glutamate, disodium undecylenoyl glutamate, potassium undecylenoyl glutamate, dipotassium undecylenoyl glutamate, disodium hydrogenated tallow glutamate, sodium stearoyl glutamate, disodium stearoyl glutamate, potassium stearoyl glutamate, sodium myristoyl glutamate, potassium myristoyl glutamate, sodium cocoyl/hydrogenated tallow glutamate, sodium cocoyl/palmoyl/sunfloweroyl glutamate, sodium hydrogenated tallowoyl glutamate, sodium olivoyl glutamate, sodium palmoyl glutamate, TEA-cocoyl glutamate, TEA-hydrogenated tallowoyl glutamate, TEA-lauroyl glutamate, and mixtures thereof.

The glutamate surfactant may be selected from the group consisting of disodium capryloyl glutamate, disodium cocoyl glutamate, disodium lauroyl glutamate, potassium capryloyl glutamate, potassium cocoyl glutamate, potassium lauroyl glutamate, potassium myristoyl glutamate, sodium capryloyl glutamate, sodium cocoyl glutamate, sodium lauroyl glutamate, sodium myristoyl glutamate, and mixtures thereof. In some examples, the glutamate surfactant may be selected from the group consisting of disodium capryloyl glutamate, disodium cocoyl glutamate, disodium lauroyl glutamate, potassium capryloyl glutamate, potassium cocoyl glutamate, potassium lauroyl glutamate, sodium capryloyl glutamate, sodium cocoyl glutamate, sodium lauroyl glutamate, and mixtures thereof.

The alaninate surfactant may be selected from the group consisting of sodium cocoyl alaninate, sodium lauroyl alaninate, sodium N-dodecanoyl-1-alaninate, TEA-cocoyl alaninate, TEA-lauroyl methyl Beta-alaninate, sodium cocoyl hydroxyethyl Beta-alaninate, sodium lauroyl hydroxyethyl Beta-alaninate, and mixtures thereof.

In some examples, the alaninate surfactant may include sodium cocoyl alaninate.

The sarcosinate surfactant may be selected from the group consisting of ammonium cocoyl sarcosinate, ammonium lauroyl sarcosinate, potassium cocoyl sarcosinate, potassium lauroyl sarcosinate, sodium lauroyl sarcosinate, sodium cocoyl sarcosinate, sodium myristoyl sarcosinate, sodium oleoyl sarcosinate, sodium palmitoyl sarcosinate, TEA-cocoyl sarcosinate, TEA-lauroyl sarcosinate, TEA-oleoyl sarcosinate, TEA-palm kernel sarcosinate, lauroyl sarcosinate, isopropyl lauroyl sarcosinate, and mixtures thereof.

The sarcosinate surfactant may be selected from the group consisting of potassium lauroyl sarcosinate, potassium cocoyl sarcosinate, sodium cocoyl sarcosinate, sodium lauroyl sarcosinate, sodium myristoyl sarcosinate, sodium palmitoyl sarcosinate, and mixtures thereof.

The sarcosinate surfactant may be selected from the group consisting of potassium lauroyl sarcosinate, potassium cocoyl sarcosinate, sodium cocoyl sarcosinate, and sodium lauroyl sarcosinate and mixtures thereof.

The sarcosinate surfactant may be selected from the group consisting of sodium cocoyl sarcosinate, and sodium lauroyl sarcosinate and mixtures thereof.

The aspartate surfactant may be selected from the group consisting of sodium lauroyl aspartate, sodium lauryl aspartate, sodium myristyl aspartate, sodium cocoyl aspartate, disodium lauroyl aspartate, di-TEA palmitoyl aspartate, potassium lauryl aspartate, potassium myristyl aspartate, and mixtures thereof.

The glycinate surfactant may be selected from the group consisting of sodium cocoyl glycinate, sodium lauroyl glycinate, potassium cocoyl glycinate, potassium lauroyl glycinate, Crosilkquat-glycine and mixtures thereof.

The anionic amino acid surfactant may be selected from the group consisting of sodium cocoyl sarcosinate, sodium lauroyl sarcosinate, sodium cocoyl alaninate, and mixtures thereof.

Alternatively, or additionally, the anionic surfactant comprises sodium laureth(n) sulfate (SLEnS), wherein n is the average moles of ethoxylation, wherein n equals to 1, 2 or 3.

In some examples, the anionic surfactant may comprise sodium laureth(n) sulfate (SLEnS), wherein n is the average moles of ethoxylation, wherein n equals to 1 (SLE1S).

The anionic surfactant may comprise a mixture of sodium laureth(3) sulfate (SLE3S) and sodium lauryl sulfate SLS.

Alternatively, the anionic surfactant may comprise a mixture of sodium laureth(1) sulfate and sodium lauryl sulfate.

In certain aspects, the personal cleansing composition may not comprise any sodium laureth(n) sulfate (SLEnS), wherein n is the average moles of ethoxylation, wherein n is equals to 0, 2 or 3.

It is understood that a material such as SLEnS, for example, can comprise a significant amount of molecules which have no ethoxylate, 1 mole ethoxylate, 2 mole ethoxylate, 3 mole ethoxylate, and so on in a distribution which can be broad, narrow or truncated from n=0 to 10. Hence, sodium laureth(1) sulfate (SLE1S) can comprise a significant amount of molecules which have no ethoxylate, 1 mole ethoxylate, 3 mole ethoxylate, and so on in a distribution which can be broad, narrow or truncated and still comprise sodium laureth(1) sulfate (SLE1S) where the average of the distribution is 1.

The personal cleansing composition may comprise from about 8% to about 12%, alternatively from about 9% to about 10%, by weight of the composition, of sodium laureth (n) sulfate SLEnS, wherein n is the average moles of ethoxylation, wherein n equals 1, 2 or 3; and from about 0.75% to about 5%, alternatively from about 1% to about 2% of an anionic amino acid surfactant by weight of the composition. The amino acid surfactant can be selected from the group consisting of sodium cocoyl sarcosinate, sodium lauroyl sarcosinate, sodium cocoyl alaninate, and mixtures thereof.

The addition of an anionic amino acid surfactant as set out hereinbefore to sodium laureth(n) sulfate (SLEnS), wherein n is the average moles of ethoxylation, wherein n equals to 1, 2 or 3, can help to enhance further the natural antimicrobial defensive ability of human skin.

The personal cleansing composition may comprise from about 0.5% to about 10% of one or more additional anionic surfactants, alternatively from about 0.75% to about 5% of one or more additional anionic surfactants, alternatively from about 1% to about 2% of one or more additional anionic surfactants by weight of the composition.

The one or more additional anionic surfactants may be selected from the group consisting of isethionate surfactants, sarcosinate surfactants, sulfosuccinate surfactants, sulfonate surfactants, sulfoacetate surfactants, glycinate surfactants, alaninate surfactants, glutamate surfactants, lactate surfactants, lactylate surfactants, glucose carboxylate surfactants, taurate surfactants, and mixtures thereof.

Suitable isethionate surfactants can include the reaction product of fatty acids esterified with isethionic acid and neutralized with sodium hydroxide. Suitable fatty acids for isethionate surfactants can be derived from coconut oil or palm kernel oil including amides of methyl tauride. Non-limiting examples of isethionates can be selected from the group consisting of sodium lauroyl methyl isethionate, sodium cocoyl isethionate, ammonium cocoyl isethionate, sodium hydrogenated cocoyl methyl isethionate, sodium lauroyl isethionate, sodium cocoyl methyl isethionate, sodium myristoyl isethionate, sodium oleoyl isethionate, sodium oleyl methyl isethionate, sodium palm kerneloyl isethionate, sodium stearoyl methyl isethionate, and mixtures thereof.

Non-limiting examples of sarcosinate surfactants can be selected from the group consisting of sodium lauroyl sarcosinate, sodium cocoyl sarcosinate, sodium myristoyl sarcosinate, TEA-cocoyl sarcosinate, ammonium cocoyl sarcosinate, ammonium lauroyl sarcosinate, dimer dilinoleyl bis-lauroylglutamate/lauroylsarcosinate, lauroyl sarcosinate, isopropyl lauroyl sarcosinate, potassium cocoyl sarcosinate, potassium lauroyl sarcosinate, sodium oleoyl sarcosinate, sodium palmitoyl sarcosinate, TEA-lauroyl sarcosinate, TEA-oleoyl sarcosinate, TEA-palm kernel sarcosinate, and mixtures thereof. The sarcosinate surfactant may be selected from the group consisting of sodium lauroyl sarcosinate, sodium cocoyl sarcosinate, and mixtures thereof.

Non-limiting examples of sulfosuccinate surfactants can include disodium N-octadecyl sulfosuccinate, disodium lauryl sulfosuccinate, diammonium lauryl sulfosuccinate, sodium lauryl sulfosuccinate, disodium laureth sulfosuccinate, tetrasodium N-(1,2-dicarboxyethyl)-N-octadecyl sulfosuccinnate, diamyl ester of sodium sulfosuccinic acid, dihexyl ester of sodium sulfosuccinic acid, dioctyl esters of sodium sulfosuccinic acid, and mixtures thereof.

Non-limiting examples of sulfonate surfactants can include alpha olefin sulfonates, linear alkylbenzene sulfonates, sodium laurylglucosides hydroxypropylsulfonate, and mixtures thereof.

Non-limiting examples of sulfoacetate surfactants can include sodium lauryl sulfoacetate, ammonium lauryl sulfoacetate, and mixture thereof.

Non-limiting examples of glycinate surfactants can include sodium cocoyl glycinate, sodium lauroyl glycinate, and mixture thereof.

Non-limiting example of lactate surfactants can include sodium lactate.

Non-limiting examples of lactylate surfactants can include sodium lauroyl lactylate, sodium cocoyl lactylate, and mixture thereof.

Non-limiting examples of glucose carboxylate surfactants can include sodium lauryl glucoside carboxylate, sodium cocoyl glucoside carboxylate, and mixtures thereof.

Co-Surfactant

The personal cleansing composition comprises from about 1% to about 15% of one or more cosurfactants, alternatively from about 1.5% to about 5% of one or more cosurfactants, alternatively from about 1.5% to about 2% of one or more cosurfactants by weight of the composition. The one or more cosurfactants may be selected from the group consisting of amphoteric surfactants, zwitterionic surfactants, and mixtures thereof.

The personal cleansing composition may include at least one of an amphoteric surfactant and a zwitterionic surfactant. Suitable amphoteric or zwitterionic surfactants can include those described in U.S. Pat. Nos. 5,104,646 and 5,106,609.

Amphoteric surfactants can include those that can be broadly described as derivatives of aliphatic secondary and tertiary amines in which an aliphatic radical can be straight or branched chain and wherein an aliphatic substituent can contain from 8 to 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378.

Alternatively or in addition, the one or more cosurfactants included in the personal cleansing composition described herein may comprise an amphoteric surfactant that is selected from the group consisting of sodium lauroamphoacetate, sodium cocoamphoacetate, disodium lauroamphoacetate, disodium cocodiamphoacetate, and mixtures thereof.

Zwitterionic surfactants suitable for use in the one or more cosurfactants of the personal cleansing composition described herein may include those that are broadly described as derivatives of aliphatic quaternary ammonium, phosphonium, and sulfonium compounds, in which the aliphatic radicals can be straight or branched chains, and wherein one of the aliphatic substituents can contain from 8 to 18 carbon atoms and one can contain an anionic group, e.g., carboxy, sulfonate, sulfate, phosphate, or phosphonate. The zwitterionic surfactant included in the personal cleansing composition described herein may include one or more betaines, including cocoamidopropyl betaine.

Alternatively, the amphoteric or zwitterionic surfactant may be selected from cocamidopropyl betaine, lauramidopropyl betaine, coco-betaine, lauryl betaine, cocoamphoacetate, cocoamphodiacetate, lauroamphoacetate, lauroamphodiacetate, lauramine oxide, sarcosinate, glutamate, lactate and mixtures thereof.

Examples of betaine zwitterionic surfactants may include coco dimethyl carboxymethyl betaine, cocoamidopropyl betaine (CAPB), coco-betaine, lauryl amidopropyl betaine (LAPB), oleyl betaine, lauryl dimethyl carboxymethyl betaine, lauryl dimethyl alpha-carboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. Examples of sulfobetaines may include coco dimethyl sulfopropyl betaine, stearyl dimethyl sulfopropyl betaine, lauryl dimethyl sulfoethyl betaine, lauryl bis-(2-hydroxyethyl) sulfopropyl betaine and mixtures thereof.

The one or more cosurfactants may comprise a zwitterionic surfactant. The zwitterionic surfactant can be a betaine and/or a sultaine. In some examples, the zwitterionic surfactant can be selected from the group consisting of cocamidopropyl betaine, lauramidopropyl betaine, cocamidopropyl hydroxysultaine and mixtures thereof. In other examples, the zwitterionic surfactant can be cocamidopropyl hydroxysultaine and/or cocamidopropyl betaine.

Nonionic surfactants suitable for use can include those selected from the group consisting of alkyl ethoxylates, alkyl glucosides, polyglucosides (e.g., alkyl polyglucosides, decyl polyglucosides), polyhydroxy fatty acid amides, alkoxylated fatty acid esters, sucrose esters, amine oxides, or mixtures thereof. Some exemplary nonionic surfactants can include cocamide monoethanolamine, decyl glucoside, or a combination thereof.

Additional surfactants and other ingredients suitable for personal cleansing compositions are found in US Pub. No. 2020/0046623, which is hereby incorporated by reference.

Organic Acid

The personal cleansing composition comprises from about 0.01% to about 1%, alternatively from about 0.02% to about 0.8%, alternatively from about 0.03% to about 0.5%, alternatively from about 0.05% to about 0.3%, alternatively from about 0.05% to about 0.15% of an organic acid having a pKa greater than about 2.7 or a cosmetically acceptable salt thereof, or a mixture thereof, by weight of the composition.

The personal cleansing composition comprises an organic acid having a pKa greater than about 2.7, alternatively a pKa from about 2.75 to about 5.0, alternatively a pKa from about 3.0 to about 4.5, or a cosmetically acceptable salt thereof, or a mixture thereof.

The cosmetically acceptable salt of the organic acid having a pKa as set out above may be sodium, potassium, calcium, magnesium, or ammonium salts.

Alternatively, the personal cleansing composition comprises an organic acid having a pKa greater than about 2.7, alternatively a pKa from about 2.75 to about 5.0, alternatively a pKa from about 3.0 to about 4.5, or a mixture thereof. The personal cleansing composition does not comprise any cosmetically acceptable salt of the organic acid.

The organic acid having a pKa greater than about 2.7 may be selected from the group consisting of 2-pyrrolidone-5-carboxylic acid (pidolic acid), adipic acid, gluconolactone acid, glutamic acid, glycolic acid, glutaric acid, tartaric acid, ascorbic acid, benzoic acid, salicylic acid, citric acid, malic acid, succinic acid, lactic acid, a cosmetically acceptable salt thereof, and mixtures thereof.

The organic acid having a pKa from about 2.75 to about 5.0 may be selected from the group consisting of 2-pyrrolidone-5-carboxylic acid (pidolic acid), adipic acid, glutamic acid, glycolic acid, glutaric acid, tartaric acid, ascorbic acid, benzoic acid, citric acid, malic acid, succinic acid, lactic acid, a cosmetically acceptable salt thereof, and mixtures thereof.

The organic acid having a pKa from about 3.0 to about 4.5 may be selected from the group consisting of 2-pyrrolidone-5-carboxylic acid, adipic acid, gluconic acid, glycolic acid, glutaric acid, ascorbic acid, benzoic acid, citric acid, malic acid, succinic acid, lactic acid, a cosmetically acceptable salt thereof, and mixtures thereof.

The organic acid having a pKa from about 3.0 to about 4.5 may be selected from the group consisting of 2-pyrrolidone-5-carboxylic acid, adipic acid, gluconic acid, glycolic acid, glutaric acid, malic acid, succinic acid, lactic acid, a cosmetically acceptable salt thereof, and mixtures thereof.

In some examples, the organic acid may comprise 2-pyrrolidone-5-carboxylic acid, or a cosmetically acceptable salt thereof, or a mixture thereof.

The cosmetically acceptable salt of 2-pyrrolidone-5-carboxylic acid may be sodium, potassium, calcium, magnesium, or ammonium salts.

The personal cleansing composition may comprise from about 0.02% to about 0.8%, alternatively from about 0.03% to about 0.5%, alternatively from about 0.05% to about 0.3%, alternatively from about 0.05% to about 0.15% of 2-pyrrolidone-5-carboxylic acid by weight of the composition.

Without wishing to be bound by theory, the organic acid as set out above can protonate the carboxylate functionalities on the phospholipid membrane of bacteria and reduce the tendency of the membrane to electronically repel anionic surfactants, thereby facilitating proper interaction between the present, anionic surfactants and the membrane.

Moreover, the organic acids as set out hereinbefore can help facilitating the creation of a low pH buffer on the surface of a substrate, thereby promoting human skin maintain its natural barrier against bacteria.

Also, the organic acids as set out hereinbefore, including 2-pyrrolidone-5-carboxylic acid, provided in a personal cleansing composition comprising the anionic surfactant and the pH as set out herein can be deposited onto skin and through skin layers.

pH

The pH of the personal cleansing composition can be from about 5.0 to about 6.5, alternatively from about 5.2 to about 6.0, alternatively from about 5.3 to about 5.8, alternatively from about 5.4 to about 5.8, alternatively 5.5 to 5.7. The pH of the personal cleansing composition can be from about 3.0 to about 6.5, preferably from about 4.0 to about 5.8, more preferably from about 4.5 to about 5.7, even more preferably from about 4.7 to about 5.7.

The pH of the skin is typically naturally acidic, namely between about 4.5 and about 6.5. An acidic skin pH can help to activating specific enzyme to regulate skin activity and to balance the acid mantle of the skin. Such balanced acid mantle of the skin together with the antimicrobial peptites (AMPs) present in the skin layers can help the skin for maintaining or improving its natural barrier against bacteria, especially against *Staphylococcus aureus*.

The personal cleansing composition may comprise an acidic pH as defined above to help the skin to reinforce its natural barrier against bacteria.

It has also been found that a pH from about 5.0 to about 6.5 could also help to improve the stability of the personal cleansing composition. As an example, the stability of the personal cleansing composition may be altered when comprising optional ingredients such as fragrances. Perfume instability can typically be observed when specific fragrances might be hydrolyzed in an acidic medium. A relatively higher pH from about 5.0 to about 6.5 can help to prevent any perfume or any pH-sensitive ingredient instability.

A variety of compounds may be used to adjust the pH value of a composition. Such suitable compounds can include, but are not limited to, acetic acid, hydrochloric acid, sodium hydroxide, magnesium hydroxide, triethylamine, diethylamine, ethylamine, monoethanol amine, and any mixtures thereof. The personal cleansing composition may comprise greater than about 0% to about 2% of the pH adjusting agent, by weight of the composition. In some examples, the pH adjusting agent can comprise citric acid.

Solubilizer

The personal cleansing composition may include one or more solubilizers such as sugar alcohols or glycols. The sugar alcohols can include sorbitol. The glycols can include propylene glycol, dipropylene glycol, polyethylene glycol, derivatives thereof, and mixtures thereof. In one example, the personal cleansing compositions can minimize the amount of solubilizers.

The personal cleansing composition may include no more than about 10%, alternatively no more than about 5%, alternatively no more than about 3%, alternatively no more than about 1%, alternatively greater than about 0% but less than about 3%, alternatively greater than about 0% but less than about 1%, by weight of the composition, of one or more solubilizers. The personal cleansing composition may be substantially free of solubilizers, alternatively the composition may be free of solubilizers.

Structurant

The personal cleansing composition may include one or more hydrophilic structurants such as carbohydrate structurants and gums. Some suitable carbohydrate structurants include raw starch (corn, rice, potato, wheat, and the like) and pregelatinized starch. Some suitable gums include carrageenan, guar gum and xanthan gum. The personal cleansing composition may include from about 0.1% to about 30%, from about 2% to about 25%, or from about 4% to about 20%, by weight of the composition, of one or more carbohydrate structurants.

Humectant

The personal cleansing composition may include one or more humectants. Examples of humectants can include polyhydric alcohols. Further, humectants such as glycerin can be included the personal cleansing composition as a result of production or as an additional ingredient. For example, glycerin can be a by-product after saponification of the cleansing composition. Including additional humectant can result in a number of benefits such as improvement in hardness of the personal cleansing composition, decreased water activity of the personal cleansing composition, and reduction of a weight loss rate of the cleansing composition over time due to water evaporation. The personal cleansing composition may comprise from greater than about 0% to about 10% of one or more humectants, by weight of the composition.

Inorganic Salt

The personal cleansing composition may include one or more inorganic salts. Inorganic salts can help to maintain a particular water content or level of the composition and improve hardness of the composition. The inorganic salts can also help to bind the water in the composition to prevent water loss by evaporation or other means. The personal cleansing composition may optionally include from about 0.01% to about 15%, alternatively from about 1% to about 12%, alternatively from about 2.5% to about 10.5%, by weight of the composition, of one or more inorganic salts. Examples of suitable inorganic salts can include magnesium nitrate, trimagnesium phosphate, calcium chloride, sodium carbonate, sodium aluminum sulfate, disodium phosphate, sodium polymetaphosphate, sodium magnesium succinate, sodium tripolyphosphate, aluminum sulfate, aluminum chloride, aluminum chlorohydrate, aluminum-zirconium trichlorohydrate, aluminum-zirconium trichlorohydrate glycine complex, zinc sulfate, ammonium chloride, ammonium phosphate, calcium acetate, calcium nitrate, calcium phosphate, calcium sulfate, ferric sulfate, magnesium chloride, magnesium sulfate, and tetrasodium pyrophosphate.

Skin Benefit Agent

The personal cleansing composition may include from about 0.5% to about 20% of one or more skin benefit agents or actives, by weight of the composition.

Examples of suitable skin benefit agents can include petrolatum, glyceryl monooleate, mineral oil, natural oils, and mixtures thereof. Additional examples of skin benefit agents can include water insoluble or hydrophobic benefit agents.

Non-limiting examples of glycerides suitable for use as hydrophobic skin benefit agents herein can include castor oil, safflower oil, corn oil, walnut oil, peanut oil, olive oil, cod liver oil, almond oil, avocado oil, palm oil, sesame oil, vegetable oils, sunflower seed oil, soybean oil, vegetable oil derivatives, coconut oil and derivatized coconut oil, cottonseed oil and derivatized cottonseed oil, jojoba oil, cocoa butter, and mixtures thereof.

Non-limiting examples of alkyl esters suitable for use as hydrophobic skin benefit agents herein can include isopropyl esters of fatty acids and long chain esters of long chain (e.g., C10-C24) fatty acids, e.g., cetyl ricinoleate, non-limiting examples of which can include isopropyl palmitate, isopropyl myristate, cetyl riconoleate, and stearyl riconoleate. Other example can include hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and mixtures thereof.

Non-limiting examples of polyglycerin fatty acid esters suitable for use as hydrophobic skin benefit agents herein can include decaglyceryl distearate, decaglyceryl diisostearate, decaglyceryl monomyriate, decaglyceryl monolaurate, hexaglyceryl monooleate, and mixtures thereof.

Preservative

The personal cleansing composition may include one or more preservatives, generally included at less than about 2% by weight of the composition, alternatively from 0.1% to 0.5% by weight of the composition. Such suitable preservatives can include, but are not limited to, benzyl alcohol, kathon, propylene glycol, hydroxy acetophenone, sodium benzoate, disodium ethylenediaminetetraacetic acid (EDTA), parabene, phenoxy ethanol, imidazolidinyl urea, and any mixture thereof. The one or more preservatives may alternatively comprise sodium benzoate, or a mixture of sodium benzoate and kathon. Kathon is composed of methylchloroisothiazolinone and methylisothiazolinone.

Optional Ingredients

As can be appreciated, the compositions described herein may include a variety of optional components to tailor the properties and characteristics of the composition. As can be appreciated, suitable optional components are well known and can generally include any components which are physically and chemically compatible with the essential components of the compositions described herein. Optional components should not otherwise unduly impair product stability, aesthetics, or performance. Individual concentrations of optional components can generally range from about 0.001% to about 10%, by weight of the composition. Optional components can be further limited to components which will not impair the clarity of a translucent composition.

Optional components may include, but are not limited to, conditioning agents (including hydrocarbon oils, fatty esters, silicones), cationic polymers, anti-dandruff actives, and chelating agents. Additional suitable optional ingredients include but are not limited to encapsulated and non-encapsulated perfumes or fragrances, colorants, particles, anti-microbials, foam boosters, anti-static agents, moisturizing agents, propellants, self-foaming agents, pH adjusting agents and buffers, preservatives, pearlescent agents, opacifiers, sensates, suspending agents, solvents, diluents, anti-oxidants, vitamins, and mixtures thereof.

The personal cleansing composition may comprise from 0.1% to 1.0%, alternatively from 0.5% to 0.6% of a fragrance, by weight of the composition.

Such optional ingredients should be physically and chemically compatible with the components of the composition, and should not otherwise unduly impair product stability, aesthetics, or performance. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein.

Antimicrobial Active

The personal cleansing composition may be substantially free of an antimicrobial active. Alternatively, the personal cleansing composition may comprise less than about 1% of an antimicrobial active, by weight of the composition. Alternatively, the personal cleansing composition may free of an antimicrobial active. Alternatively, the personal cleansing composition may comprise less than about 0.1% of an antimicrobial active.

However, in some aspects, the personal cleansing composition may comprise an antimicrobial active. The antimicrobial active may be piroctone olamine.

A personal cleansing composition may be provided and may comprise:

(a) from about 1% to about 15% of an anionic surfactant by weight of the composition, wherein the anionic surfactant comprises sodium laureth(n) sulfate (SLEnS), wherein n is the average moles of ethoxylation, wherein n equals to 1, 2 or 3, preferably sodium laureth(n) sulfate (SLEnS), wherein n is the average moles of ethoxylation, wherein n equals to 1;

(b) from about 0.01% to about 1% of an organic acid having a pKa greater than about 2.7, preferably a pKa from about 2.75 to about 5, alternatively a pKa from about 3 to about 4.5, or a cosmetically acceptable salt thereof, or a mixture thereof, by weight of the composition;

(c) an antimicrobial active, preferably wherein the antimicrobial active is piroctone olamine; and wherein the pH of the personal cleansing composition is from 3.5 to 6.5, preferably from about 5.0 to about 6.5.

The personal cleansing composition may comprise from about 0.01% to about 2%, alternatively from about 0.1% to about 0.75%, alternatively from about 0.2% to about 0.5% of piroctone olamine, by weight of the composition.

The personal cleansing composition as set out just above may be used for helping human skin maintain or enhance its natural barrier against bacteria, especially against *Staphylococcus aureus*.

Method

A non-therapeutic method for maintaining or improving the natural antimicrobial defense ability of human skin against bacteria, especially against *Staphylococcus aureus*, is provided and comprises the step of applying onto the human skin the personal cleansing composition as set out hereinbefore, following by rinsing off the composition.

Alternatively, a non-therapeutic method for promoting the skin natural defense efficacy against bacteria is provided and comprises the step of applying onto the human skin the personal cleansing composition as set out hereinbefore, following by rinsing off the composition.

A method for maintaining or restoring the natural skin pH is also provided and comprises the step of applying onto the human skin the personal cleansing composition as set out hereinbefore, following by rinsing off the composition.

Skin surface pH contributes to the skin natural antimicrobial barrier. If the acid mantel of the skin is damaged/impaired, natural skin protection function will be impacted. A treatment with a personal cleansing composition as set out hereinbefore that can help for protecting, maintaining or even further restoring the natural skin pH.

Forms and Uses

Product Form

The personal cleansing composition may be presented in typical personal cleansing formulations. They may be in the form of solutions, dispersion, emulsions, foams, and other delivery mechanisms. The personal cleansing composition may be a rinse-off composition.

The personal cleansing composition may be extrudable or dispensable from a single chamber package. The personal cleansing compositions can be in the form of liquid, semi-liquid, cream, lotion or gel, or solid compositions intended for topical application to skin.

Examples of personal cleansing compositions can include but are not limited to body wash, moisturizing body wash, foaming body wash, shower gels, a shower or bath cream, skin cleansers, cleansing milks, body wash, in shower body moisturizer, gel, emulsion, oil, mousse or spray.

The personal cleansing composition may be not in the form of a liquid hand wash or a liquid hand sanitizer.

The product forms contemplated for purposes of defining the personal cleansing compositions and methods are rinse-off formulations by which it is meant that the product is applied topically to the skin and then subsequently (i.e., within minutes) rinsed away with water, or otherwise wiped off using a substrate or other suitable removal means.

Uses

The personal cleansing composition as set out herein-above may be used for maintaining or improving the natural antimicrobial defense ability of human skin, preferably against *Staphylococcus aureus*.

The personal cleansing composition as set out herein-above may be used for promoting the skin natural defense efficacy.

The personal cleansing composition as set out herein-above may be used for maintaining or restoring the natural skin pH.

The personal cleansing composition as set out hereinbe-fore may be used for balancing skin pH and retaining skin moisture.

The personal cleansing composition as set out herein-above may be used for depositing an organic acid as defined hereinabove onto skin or through the skin layers. In some examples, the organic acid can be 2-pyrrolidone-5-carbox-ylic acid.

All the limitations and aspects as disclosed hereinabove for the personal cleansing composition might apply herein below.

A personal cleansing composition is provided and com-prises:

(a) from 1% to 15% of an anionic surfactant by weight of the composition, wherein the anionic surfactant com-prises sodium laureth(n) sulfate (SLEnS), wherein n is the average moles of ethoxylation, wherein n equals to 1, 2 or 3;

(b) from 0.01% to 1% of an organic acid having a pKa greater than 2.7, preferably a pKa from 2.75 to 5, alternatively a pKa from 3 to 4.5, or a cosmetically acceptable salt thereof, or a mixture thereof, by weight of the composition; and wherein the pH of the personal cleansing composition is from 5.0 to 6.5; for use in a method of maintaining or improving the natural anti-microbial defense ability of human skin against bacte-ria, preferably against *Staphylococcus aureus*.

Such personal cleansing composition can help for deliv-ering long-lasting-deep layer skin protection, namely up to 12 hours, for 3 skin layers, against opportunistic pathogenic microorganisms, preferably against *Staphylococcus aureus*.

A personal cleansing composition is also provided and comprises:

(a) from 1% to 15% of an anionic surfactant by weight of the composition, wherein the anionic surfactant com-prises sodium laureth(n) sulfate (SLEnS), wherein n is the average moles of ethoxylation, wherein n equals to 1, 2 or 3;

(b) from 0.01% to 1% of an organic acid having a pKa greater than 2.7, preferably a pKa from 2.75 to 5, more preferably a pKa from 3 to 4.5, or a cosmetically acceptable salt thereof, or a mixture thereof, by weight of the composition; and wherein the pH of the personal cleansing composition is from 5.0 to 6.5; in a method of maintaining or improving the natural antimicrobial defense ability of human skin against bacteria, preferably against *Staphylococcus aureus*; characterized in that the personal cleansing composition is applied onto the human skin following by rinsing off the composition.

TEST METHODS

It is understood that the Test Methods that are disclosed in the Test Methods Section of the present application should be used to determine the respective values of the parameters of Applicants' invention as such invention is described and claimed herein.

Cone/Plate Viscosity Measurement

The viscosity of the personal cleansing composition is measured by a Cone/Plate Controlled Stress Brookfield Rheometer R/S Plus, by Brookfield Engineering Laborato-ries, Stoughton, MA The cone used (Spindle C-75-1) has a diameter of 75 mm and 1° angle. The viscosity is determined using a steady state flow experiment at constant shear rate of $2 \text{ s}^{-1}$ and at temperature of 26.5° C. The sample size is 2.5 mL and the total measurement reading time is 3 minutes.

Measuring Residual Antimicrobial Efficacy of a Product

The protocol provides a non-invasive method for evalu-ating the residual antimicrobe efficacy of a personal cleans-ing composition against designated bacteria. The method includes in vivo product application, skin stratum corneum sampling via tape stripping, germ challenge test on skin samples on the tape strip, and germ load quantification via Soleris® Detection time (DT).

The test organism is *Staphylococcus aureus* (ATCC® 6538/ATCC® 27127). Ideally, the strain is within 5 genera-tions and has a routine identification at a frequency as makes sense for the bacteria and the test.

The test organism is prepared for the study. For *S. aureus*, refresh the test organism by streaking on a trypticase soy agar (TSA) plate and growing 18-24 hrs. On the second day, inoculate 1 colony of organism in a 50 mL tube containing 30 mL trypticase soy broth (TSB), and grow at 35±2° C. for 18 hours±15 min. On the test day, dilute the above bacteria culture by 1:10 or other concentrations to new TSB (e.g. 0.5 mL culture to 4.5 mL TSB media). The test organism culture is used within half an hour for inoculating tape strips for all samples tested.

A) Product Treatment and Sampling Protocol

A target demographic is selected for testing, for example healthy individuals ages 20-60 inclusive. Six to seven dif-ferent subjects are tested. The subjects can be instructed to have a wash out period. For example, the wash out period can be to wash with a prescribed soap for 5 days, shower on day 6 with City Water only, and to refrain from taking a shower on day 7.

After the wash out period, a baseline skin sample may be taken on the target site prior to any product application. This is recorded as timepoint baseline. Then, the subjects are either instructed on how to do the following steps or a trained professional may do the steps on the subject. Utilizing tap water with a temperature of 35° C.+/−2° C. and a water flow rate of 4.0 L/min+/−0.3 L/min wet the volar surface of the forearm under the running water. For the liquid products tested herein, 0.7 mL of product was dispensed on the test subject's forearm and spread evenly for 15 seconds. If necessary, continue to rub the lather on the forearm using the same up-and-down motion from the wrist to the elbow, for an additional 45 seconds. Rinse the forearm for 15 seconds by holding the arm under the running water. Do not rub the arm during rinsing. Remove the arm from the running water. Pat the arm dry with a paper towel without rubbing. The site is now ready for skin sampling with an adhesive. This is recorded as timepoint zero hour. The above steps are repeated three times on the same day before sampling.

Once the target site, here the arm, is ready for sampling, after the third wash, a strip of adhesive tape is adhered to the forearm avoiding folds. The skin site of interest is marked in advance for consistency. To keep uniform pressure and reach optimal adhesive bond, a roller can be used to press the tape onto the skin surface (ex. twice on each site). Then, the tapes were peeled off from the skin and placed on the surface of a TSA agar plate with the skin sample side up. The tape strips can also be inoculated prior to being placed on the TSA agar plate.

B) Prepping and Testing with an Optical Detection Method (Ex. Soleris®)

Inoculate 10 μL of the tested microorganism culture on the skin sample side of each tape strip. Spread evenly over the tape surface, for example, with a sterile inoculation loop or pipette tip. Use one inoculation loop or pipette tip for each tape strip, and discard inoculation loop or pipette tip after use. Allow the inoculum to visually dry on the surface of the tape strip (approximately ~3-5 minutes).

The inoculated test strips can then be prepped for sampling measurement depending on what is intended to be measured. For example, if the inoculated test strips are going to be run through an optical analysis for detection of microbial growth, then the inoculated tape strip residing on the TSA agar plate is placed into a humidified incubator at 35° C. and 60%±20% relative humidity until time of collection (e.g. baseline=immediately before washing, t=0 is immediately after washing, t=3 is three hours after washing).

At each sampling time, aseptically transfer each tape into one NF-TVC (non-fermenting total viable count) vial for continuous monitoring for 24 hours to determine the detection times (DTs). Soleris parameters can be set as: Temperature 34° C.; Threshold: 10; Shuteye: 25; Skip 1. The detection time can be converted to the log CFU count by generating a standard calibration curve of DT vs. Log CFU.

C) Data Analysis:

The detection time was measured for each subject at each timepoint (baseline and zero hour). In the first step, delta detection time was calculated by subtraction of the baseline by zero hour. In the second step, mean delta detection time value was calculated based on the testing leg. Finally, the delta [delta detection time] value was calculated by the difference between the two testing legs.

Multiple Layer Test with 12 Hours Detection Time:

The same protocol for providing a non-invasive method for evaluating the residual antimicrobe efficacy of a personal cleansing composition against designated bacteria was used. The same wash out as set out above was carried out.

After the wash out period, a baseline skin sample may be taken on the target site prior to any product application. This is recorded as timepoint baseline. Then, the subjects are either instructed on how to do the following steps or a trained professional may do the steps on the subject. Utilizing tap water with a temperature of 35° C.+/−2° C. and a water flow rate of 4.0 L/min+/−0.3 L/min wet the volar surface of the forearm under the running water. For the liquid products tested herein, 0.7 mL of product was dispensed on the test subject's forearm and spread evenly for 15 seconds. Then, continue to rub the lather on the forearm using the same up-and-down motion from the wrist to the elbow, for an additional 45 seconds. Rinse the forearm for 15 seconds by holding the arm under the running water. Do not rub the arm during rinsing. Remove the arm from the running water. Pat the arm dry with a paper towel without rubbing. Then, repeat this step for another two times. Totally, there are three washes. After that, the skin site is ready for sampling. This sampling timepoint is recorded as timepoint zero hour. After that, wait for 12 hours without any treatment. And then do the skin sampling (adhesive tape) and this is recorded as 12 hours timepoint.

In this study, three layers timepoint baseline and twelve hours skin samples were taken for detection time measurement. Those three layers of skin sample were taken from the same location using three different tapes. This means that the $2^{nd}$ layer was beneath the $1^{st}$ layer and the $3^{rd}$ layer was beneath the $2^{nd}$ layer.

Any skin pH measurement was performed before the $1^{st}$ layer was taken and after the $3^{rd}$ layer was taken.

Once the target site, here the arm, is ready for sampling, after the third wash, a first strip of adhesive tape is adhered to the first layer of the forearm avoiding folds. The skin site of interest can be marked in advance for consistency. To keep uniform pressure and reach optimal adhesive bond, a roller can be used to press the tape onto the skin surface (ex. twice on each site). Then, the tapes were peeled off from the skin and placed on the surface of a TSA agar plate with the skin sample side up. The tape strips can also be inoculated prior to being placed on the TSA agar plate. Then, another strip of adhesive tape is adhered at the same location to the second layer and the second tape strip is proceed like above. Finally, another strip of adhesive tape is adhered at the same location to the third layer and the third tape strip is proceed like above.

Data Analysis for Detection Time:

The detection time was measured for each subject at each timepoint (baseline and 12 hours). In the first step, detection time was calculated by subtraction of the blank tape of baseline and 12 hours, by skin tape detection time at baseline and 12 hours, respectively. This is to normalize the bacteria difference at 12 hours and baseline. In the second step, mean delta detection time is calculated by subtraction of baseline by 12 hours. Finally, the delta [delta detection time] value was calculated by the difference between the two testing legs.

Skin pH Measurement

The following Skin pH meter—HI 99181 with HI1414 probe (Hanna instruments) has been used.

Start-Up:

1. Carefully remove the protective cap. Gently wash the end of the probe with distilled water.
2. Store the probe in distilled water between measurements.

19

20

Calibration:

The following calibration needs to be done at the beginning of each testing day.

1. Turn on the pH probe with the switch at the top.
2. Open a pH 4.01 packet and place the pH probe in the bag.
3. Hold the probe in the solution until the reading stabilizes (approx. 1 min).
4. Using the small screwdriver, adjust the small "4/10" screw until the readout says 4.01.
5. Rinse the probe in distilled water.
6. Open a pH 7.01 packet and place the pH probe in the bag.
7. Hold the probe in the solution until the reading stabilizes (approx. 1 min).
8. Using the small screwdriver, adjust the small "7" screw until the readout says 7.01.
9. Rinse and store the probe in distilled water.

Subject Measurement:

For a single skin layer test after recording the timepoint zero hour, any skin pH measurement was performed before any strip of adhesive tape is adhered to the single skin layer.

For a multiple skin layer test after recording the timepoint 12 hours, any skin pH measurement was performed before any strip of adhesive tape is adhered to the Pt layer was taken and after the $3^{rd}$ layer was taken.

1. To take a measurement, remove the probe from the distilled water, leaving the end of the probe damp.
2. Place vertically on the skin area to be measured.
3. Wait for the measurement to stabilize (10-20 sec).
4. Record the value displayed to one decimal place. (e.g., "5.2")

5. Return probe to the distilled water between measurements.

Product pH Measurement

First, calibrate the Thermo Scientific Orion 320 pH meter. Do this by turning on the pH meter and waiting for 30 seconds. Then, take the electrode out of the storage solution, rinse the electrode with distilled water, and carefully wipe the electrode with a scientific cleaning wipe, such as a Kimwipe®. Submerse the electrode in the pH 7 buffer and press the calibrate button. Wait until the pH icon stops flashing and press the calibrate button a second time. Rinse the electrode with distilled water and carefully wipe the electrode with a scientific cleaning wipe. Then submerse the electrode into the pH 4 buffer and wait until the pH icon stops flashing and press the measure button. Rinse the electrode with distilled water and carefully wipe with a scientific cleaning wipe. Now the pH meter is calibrated and can be used to test the pH of a solution.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

The following examples were prepared:

Compositions (wt. %)

| Ingredients (wt. %) | Comp. Ex. 1 | Ex. 1 | Ex. 2 | Ex. 3 | Ex. 4 | Ex. 5 |
|---|---|---|---|---|---|---|
| Sodium lauryl ether (1) sulfate[1] | 9.35 | 9.35 | 9.35 | 9.35 | 9.35 | 9.35 |
| Sodium lauroyl sarcosinate[2] | — | — | — | 1.0 | — | — |
| Sodium cocoyl alaninate[3] | — | — | — | — | — | 1.0 |
| Cocamidopropyl betaine[4] | 1.65 | 1.65 | 1.65 | 1.65 | 1.65 | 1.65 |
| 2-pyrrolidone-5-carboxylic acid[5] | — | 0.1 | 0.1 | 0.1 | — | 0.1 |
| Malic acid[6] | — | — | — | — | 0.1 | — |
| Sodium benzoate[7] | 0.45 | 0.45 | 0.45 | 0.45 | 0.45 | 0.45 |
| Citric acid powder[8] | q.s. pH 5.7 | q.s. pH 5.0 | q.s. pH 5.7 | q.s. pH 5.7 | q.s. pH 5.7 | q.s. pH 5.7 |
| Preservative (Kathon; Supplier Rohm & Haas) | 0.05 | 0.05 | 0.05 | 0.05 | 0.05 | 0.05 |
| EDTA[9] | 0.10 | 0.10 | 0.10 | 0.10 | 0.10 | 0.10 |
| Fragrance | 0.60 | 0.60 | 0.60 | 0.60 | 0.60 | 0.60 |
| Sodium chloride[10] | q.s. to 8 Pa · s-10 Pa · s | q.s. to 8 Pa · s-10 Pa · s | q.s. to 8 Pa · s-10 Pa · s | q.s. to 8 Pa · s-10 Pa · s | q.s. to 8 Pa · s-10 Pa · s | q.s. to 8 Pa · s-10 Pa · s |
| water | Balance to 100 | Balance to 100 | Balance to 100 | Balance to 100 | Balance to 100 | Balance to 100 |

| Ingredients (wt. %) | Ex. 6 | Ex. 7 | Ex. 8 | Ex. 9 |
|---|---|---|---|---|
| Sodium lauryl ether (1) sulfate[1] | — | — | — | — |
| Sodium lauroyl sarcosinate[2] | 9.35 | — | 9.35 | — |
| Sodium cocoyl alaninate[3] | — | 9.35 | — | 9.35 |
| Cocamidopropyl betaine[4] | 1.65 | 1.65 | 1.65 | 1.65 |
| 2-pyrrolidone-5-carboxylic acid[5] | 0.1 | 0.1 | | — |
| Malic acid[6] | — | — | 0.1 | 0.1 |
| Sodium benzoate[7] | 0.45 | 0.45 | 0.45 | 0.45 |
| Citric acid powder[8] | q.s. pH 5.0 | q.s. pH 5.7 | q.s. pH 5.7 | q.s. pH 5.7 |
| Preservative (Kathon; Supplier Rohm & Haas) | 0.05 | 0.05 | 0.05 | 0.05 |
| EDTA[9] | 0.10 | 0.10 | 0.10 | 0.10 |
| Fragrance | 0.60 | 0.60 | 0.60 | 0.60 |
| Sodium chloride[10] | q.s. to 8 Pa · s-10 Pa · s | q.s. to 8 Pa · s-10 Pa · s | q.s. to 8 Pa · s-10 Pa · s | q.s. to 8 Pa · s-10 Pa · s |

-continued

| water | Balance to 100 | Balance to 100 | Balance to 100 | Balance to 100 |

Definitions of Components
*[1]Sodium laureth(1) sulfate; Supplier Procter & Gamble Co.
*[2]Sodium lauroyl sarcosinate; Supplier Tinci
*[3]Sodium cocoyl alaninate; Supplier Tinci
*[4]Cocamidopropyl Betaine; Supplier Tinci
*[5]2-pyrrolidone-5-carboxylic acid; Supplier Longteng
*[6]Malic acid; Supplier Merck Sigma-Aldrich
*[7]Sodium benzoate; Supplier Wuhan Youji Industries
*[8]Citric acid powder; Supplier Yixing Union Biochemical
*[9]EDTA (Disodium Ethylene Diamine Tetraacetic Acid); Supplier Shijiazhuang Jackchem Co
*[10]Sodium chloride; Supplier China Salt Dongxing
q.s.: sufficient quantity Results:

Example 2 has been compared to Comparative Example 1 which does not comprise any organic acid having a pKa greater than 2.7 such as 2-pyrrolidone-5-carboxylic acid.

| | Delta detection time (zero hour – baseline) |
|---|---|
| Comp. Ex. 1 (no PCA) | 1.93 |
| Ex. 2 (with PCA) | 2.33 |
| Delta [Delta detection time (C. Ex. 1 – Ex. 2)] | –0.4 |

The Delta detection time increased for Ex. 2 versus Comp. Ex. 1. Hence, the addition of 0.1% PCA can help to improve the natural antimicrobial defensive ability of human skin or, in other words the skin natural defense efficacy against bacteria such as *Staphylococcus aureus*.

| | Delta skin pH (zero hour – baseline) |
|---|---|
| Comp. Ex. 1 (no PCA) | 2.15 |
| Ex. 2 (with PCA) | 2.06 |
| Delta [Delta skin pH (C. Ex. 1 – Ex. 2)] | 0.09 |

Skin surface pH contributes to the skin natural antimicrobial barrier. If the acid mantle of the skin is damaged/impaired, natural skin protection function will be impacted. A decrease of the Delta skin pH for Ex. 2 compared to Comp. Ex. 1 means that the skin pH has been protected, maintained and better restored to the natural skin pH after using the personal cleansing composition of Ex. 2 compared to Comp. Ex. 1. The addition of an organic acid having a pKa greater than 2.7 such as 2-pyrrolidone-5-carboxylic acid can help for restoring to the natural skin pH.

Example 2 has been compared to Example 1. The two examples differs from the pH of the personal cleansing composition.

| | Delta detection time (zero hour – baseline) |
|---|---|
| Ex. 2 (pH is 5.7) | 2.03 |
| Ex. 1 (pH is 5.0) | 2.38 |
| Delta [Delta detection time (Ex. 2 – Ex. 1)] | –0.35 |

The Delta detection time increased for Ex. 1 versus Ex. 2. Hence, a pH from 5.0 to 6.5, alternatively from 5.0 to 5.5 can help to improve the natural antimicrobial defensive ability of human skin or, in other words the skin natural defense efficacy against bacteria such as *Staphylococcus aureus*.

| | Delta skin pH (zero hour – baseline) |
|---|---|
| Ex. 2 (pH is 5.7) | 2.51 |
| Ex. 1 (pH is 5.0) | 2.28 |
| Delta [Delta skin pH (Ex. 2 – Ex. 1)] | 0.23 |

Skin surface pH contributes to the skin natural antimicrobial barrier. If the acid mantle of the skin is damaged/impaired, natural skin protection function will be impacted. A decrease of the Delta skin pH of Ex. 1 versus Ex. 2 means that the skin pH has been protected, maintained and better restored to the natural skin pH after using the personal cleansing composition of Ex. 1 (pH is 5.0) compared to Ex. 2 (pH is 5.7). The pH of the personal cleansing composition of 5.0 can help for restoring the natural skin pH over a pH of the personal cleansing composition of 5.7.

Multiple layers test has been performed to compare Ex. 1 comprising 0.1 wt. % of an organic acid having a pKa greater than 2.7 such as 2-pyrrolidone-5-carboxylic acid at a pH of 5.0 to a commercially available cleanser: Lux Fine Fragrance Body Wash.

Lux Fine Fragrance Body Wash is available via the Database GNPD [Online] Mintel; July 2019 (2019-07) "Lux Fine Fragrance Shining Icy Cool Refreshing Body Wash", Database accession no. 6740059:
https://www.gnpd.com/sinatra/recordpage/6740059/

Lux Fine Fragrance Shining Icy Cool Refreshing Body Wash comprises the following list of ingredients: water, myristic acid, lauric acid, potassium hydroxide, potassium chloride, sodium laureth sulfate, palmitic acid, propylene glycol, fragrance, ethylene glycol distearate, cocamidopropyl betaine, phenoxyethanol, menthol, hydroxypropyl methylcellulose, tetrasodium EDTA, butylated hydroxytoluene, piroctone olamine, manicouagan clay, *Cananga odorata* (ylang ylang) flower oil, CI 74160, CI 51319.

The measured pH of Lux Fine Fragrance Shining Icy Cool Refreshing Body Wash was 9.21 according to the Product pH Measurement test method as set out herein.

Thus, Lux Fine Fragrance Shining Icy Cool Refreshing Body Wash comprises at least: sodium laureth sulfate and the following organic acids: myristic acid, lauric acid, palmitic acid.

| Layer | | Delta detection time (12 hours – baseline) |
|---|---|---|
| 1 | Ex. 1: 0.1% PCA and pH 5.0 | 1.61 |
| 1 | C. Ex. A: Lux Fine Fragrance Body Wash | 0.34 |
| 1 | Delta [Delta detection time (Ex. 1 – C. Ex. A)] | 1.28 |

-continued

| Layer | | Delta detection time (12 hours – baseline) |
|---|---|---|
| 2 | Ex. 1: 0.1% PCA and pH 5.0 | 0.91 |
| 2 | C. Ex. A: Lux Fine Fragrance Body Wash | –0.05 |
| 2 | Delta [Delta detection time (Ex. 1 – C. Ex. A)] | 0.96 |
| 3 | Ex. 1: 0.1% PCA and pH 5.0 | 0.31 |
| 3 | C. Ex. A: Lux Fine Fragrance Body Wash | 0.02 |
| 3 | Delta [Delta detection time (Ex. 1 – C. Ex. A)] | 0.29 |

In each skin layer, the Delta detection time increased for Ex. 1 versus Comp. Ex. A—commercially available cleanser: Lux Fine Fragrance Body Wash. Hence, a personal cleansing composition as recited in the claims can help to improve the natural antimicrobial defensive ability of human skin or, in other words the skin natural defense efficacy. It is believed that an organic acid having a specific pKa greater than about 2.7, such as 2-pyrrolidone-5-carboxylic acid at a pH of 5.0 versus a pH of 9.2 can penetrate at least three layers into the skin, which can provide a deep layer of protection to users for at least about 12 hours.

The pH value was calculated based on the same procedure described above

| Layer | | Delta skin pH (12 hours – baseline) |
|---|---|---|
| 1 | Ex. 1: 0.1% PCA and pH 5.0 | 0.60 |
| 1 | C. Ex. A: Lux Fine Fragrance Body Wash | 0.77 |
| 1 | Delta [Delta skin pH (Ex. 1 – C. Ex. A)] | –0.18 |
| 3 | Delta pH Ex. 1: 0.1% PCA and pH 5.0 | 0.16 |
| 3 | Delta pH B: LUX sparkling soap based BW | 0.38 |
| 3 | Delta [Delta skin pH (Ex. 1 – C. Ex. A)] | –0.22 |

Skin surface pH contributes to the skin natural antimicrobial barrier. A decrease of the Delta skin pH at each layer for Ex. 1 versus C. Ex. A means that the skin pH has been protected, maintained and better restored to the natural skin pH.

The personal cleansing composition of Ex. 1 can help for restoring the natural skin pH compared to Comp. Ex. A (Lux Fine Fragrance Body Wash).

Effect of the Anionic Surfactant:

Example 2 (sodium lauryl ether (1) sulfate) has been compared to Example 3 in which the anionic surfactant now comprises a mixture of sodium lauryl ether (1) sulfate with sodium lauroyl sarcosinate as the anionic amino acid surfactant.

| | Delta detection time (zero hour – baseline) |
|---|---|
| Ex. 3 (SLE1S + sodium lauroyl sarcosinate) | 2.36 |
| Ex. 2 (sodium lauryl ether (1) sulfate) | 2.08 |
| Delta [Delta detection time (Ex. 3 – Ex. 2)] | 0.28 |

Example 2 (sodium lauryl ether (1) sulfate) has been compared to Example 5 in which the anionic surfactant now comprises a mixture of sodium lauryl ether (1) sulfate with sodium cocoyl alaninate as the anionic amino acid surfactant.

| | Delta detection time (zero hour – baseline) |
|---|---|
| Ex. 5 (SLE1S + sodium cocoyl alaninate) | 2.90 |
| Ex. 2 (sodium lauryl ether (1) sulfate) | 2.23 |
| Delta [Delta detection time (Ex. 5 – Ex. 2)] | 0.67 |

The Delta detection time increased for Ex. 3 or Ex. 5 versus Ex. 2. Hence, the addition of an anionic amino acid surfactant such as sodium lauroyl sarcosinate or sodium cocoyl alaninate can help to improve the natural antimicrobial defensive ability of human skin or, in other words the skin natural defense efficacy.

| | Delta skin pH (zero hour – baseline) |
|---|---|
| Ex. 3 (SLE1S + sodium lauroyl sarcosinate) | 2.30 |
| Ex. 2 (sodium lauryl ether (1) sulfate) | 2.33 |
| Delta [Delta skin pH (Ex. 3 – Ex. 2)] | –0.03 |

| | Delta skin pH (zero hour – baseline) |
|---|---|
| Ex. 5 (SLE1S + sodium cocoyl alaninate) | 2.03 |
| Ex. 2 (sodium lauryl ether (1) sulfate) | 2.25 |
| Delta [Delta skin pH (Ex. 5 – Ex. 2)] | –0.22 |

The Delta skin pH decreases when the skin is treated with the composition of Ex. 3 or Ex. 5 versus Ex. 2. Hence, the addition of an anionic amino acid surfactant such as sodium lauroyl sarcosinate or sodium cocoyl alaninate can help to protect, maintain and better restore the natural skin pH.

Additional Examples/Combinations

A. A personal cleansing composition comprising:
   (a) from 1% to 20% of an anionic surfactant by weight of the composition, wherein the anionic surfactant comprises an anionic amino acid surfactant and/or sodium laureth(n) sulfate (SLEnS), wherein n is the average moles of ethoxylation, wherein n equals to 1, 2 or 3;
   (b) from 0.01% to 1% of an organic acid having a pKa greater than 2.7, preferably a pKa from 2.75 to 5, more preferably a pKa from 3 to 4.5, or a cosmetically acceptable salt thereof, or a mixture thereof, by weight of the composition; and wherein the pH of the personal cleansing composition is from 3 to 6.5.
B. Use of the personal cleansing composition as set out hereinbefore for maintaining or improving the natural antimicrobial defense ability of human skin, preferably against *Staphylococcus aureus*.
C. A non-therapeutic method for use in a method of maintaining or enhancing the natural antimicrobial defense ability of human skin against bacteria, preferably against *Staphylococcus aureus*, comprising the step of applying onto the human skin the personal cleansing composition as set out hereinbefore, following by rinsing off the composition.
D. Use of the personal cleansing composition as set out hereinbefore for promoting the skin natural defense efficacy, preferably against *Staphylococcus aureus*.
E. A non-therapeutic method for promoting the skin natural defense efficacy against bacteria, preferably against *Staphylococcus aureus*, comprising the step of applying onto the human skin the personal cleansing composition as set out hereinbefore, following by rinsing off the composition.

F. Use of the personal cleansing composition as set out hereinbefore for maintaining or restoring the natural skin pH.

G. A method for maintaining or restoring the natural skin pH comprising the step of applying onto the human skin the personal cleansing composition as set out hereinbefore, following by rinsing off the composition.

H. A personal cleansing composition comprising:

(a) from 1% to 15% of an anionic surfactant by weight of the composition, wherein the anionic surfactant comprises sodium laureth(n) sulfate (SLEnS), wherein n is the average moles of ethoxylation, wherein n equals to 1, 2 or 3;

(b) from 0.01% to 1% of an organic acid having a pKa greater than 2.7, preferably a pKa from 2.75 to 5, more preferably a pKa from 3 to 4.5, or a cosmetically acceptable salt thereof, or a mixture thereof, by weight of the composition; and wherein the pH of the personal cleansing composition is from 5.0 to 6.5; for use in a method of maintaining or improving the natural antimicrobial defense ability of human skin against bacteria, preferably against *Staphylococcus aureus*.

I. A personal cleansing composition comprising:

(a) from 1% to 15% of an anionic surfactant by weight of the composition, wherein the anionic surfactant comprises sodium laureth(n) sulfate (SLEnS), wherein n is the average moles of ethoxylation, wherein n equals to 1, 2 or 3;

(b) from 0.01% to 1% of an organic acid having a pKa greater than 2.7, preferably a pKa from 2.75 to 5, more preferably a pKa from 3 to 4.5, or a cosmetically acceptable salt thereof, or a mixture thereof, by weight of the composition; and wherein the pH of the personal cleansing composition is from 5.0 to 6.5; in a method of maintaining or improving the natural antimicrobial defense ability of human skin against bacteria, preferably against *Staphylococcus aureus*; characterized in that the personal cleansing composition is applied onto the human skin following by rinsing off the composition.

J. A personal cleansing composition comprising:

(a) from 1% to 20% of an anionic surfactant by weight of the composition, wherein the anionic surfactant comprises an anionic amino acid surfactant and/or sodium laureth(n) sulfate SLEnS, wherein n is the average moles of ethoxylation, wherein n equals to 1, 2 or 3;

(b) from 0.01% to 1% of an organic acid having a pKa greater than 2.7, preferably a pKa from 2.75 to 5, more preferably a pKa from 3 to 4.5, or a cosmetically acceptable salt thereof, or a mixture thereof, by weight of the composition; and wherein the pH of the personal cleansing composition is from 3.0 to 6.5; in a method of maintaining or enhancing the natural defensive ability of human skin against bacteria, preferably against *Staphylococcus aureus*; characterized in that the personal cleansing composition is applied onto the human skin following by rinsing off the composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal cleansing composition comprising:

(a) from about 9% to 10% of an anionic surfactant by weight of the composition, wherein the anionic surfactant comprises sodium laureth (n) sulfate, wherein n is the average moles of ethoxylation, wherein n equals 1, 2, or 3;

(b) from about 0.01% to about 1% of an organic acid, by weight of the composition, wherein the organic acid comprises 2-pyrrolidone-5-carboxylic acid; and wherein the personal cleansing composition is a body wash or a body gel;

wherein the pH of the personal cleansing composition is from about 5.0 to about 5.5;

wherein the personal cleansing composition further comprises from about 1% to about 15% of cocamidopropyl betaine.

2. The personal cleansing composition of claim 1, wherein the personal cleansing composition comprises a delta detection time of about 2.0 to about 3.0.

3. The personal cleansing composition of claim 2, wherein the composition comprises from about 0.02% to about 0.8% of 2-pyrrolidone 5-carboxylic acid, by weight of the composition.

4. The personal cleansing composition of claim 1, wherein the composition comprises between about 1.5% to about 5% of the one or more co-surfactants.

5. The personal cleansing composition of claim 1, wherein the personal cleansing composition comprises less than 1% of an antimicrobial active, by weight of the composition.

6. The personal cleansing composition of claim 1, wherein the composition comprises from about 0.5% to about 10% of an additional anionic surfactant, by weight of the composition.

7. The personal cleansing composition of claim 6, wherein the additional anionic surfactant is chosen from the group consisting of isethionate surfactants, sarcosinate surfactants, sulfosuccinate surfactants, sulfonate surfactants, sulfoacetate surfactants, glycinate surfactants, alaninate surfactants, glutamate surfactants, lactate surfactants, lactylate surfactants, glucose carboxylate surfactants, taurate surfactants, and mixtures thereof, preferably wherein the additional anionic surfactant is selected from the group consisting of sodium cocoyl alaninate, sodium lauroyl sarcosinate, sodium cocoyl sarcosinate, or mixtures thereof.

8. The personal cleansing composition of claim 4, wherein the one or more cosurfactants comprise a zwitterionic surfactant.

9. A non-therapeutic method for helping human skin maintain, or enhance, its natural defensive ability against bacteria, against *Staphylococcus aureus*, comprising the step of applying onto the human skin the personal cleansing composition of claim 1 following by rinsing off the composition.

10. The personal cleansing composition of claim 1, wherein the personal cleansing composition further comprises:

from about 0.75% to about 5% of an anionic amino acid surfactant by weight of the composition; wherein the anionic amino acid surfactant is chosen from the group consisting of sodium cocoyl sarcosinate, sodium lauroyl sarcosinate, sodium cocoyl alaninate, or mixtures thereof.

\* \* \* \* \*